US010453561B2

(12) United States Patent
Balignasay et al.

(10) Patent No.: US 10,453,561 B2
(45) Date of Patent: Oct. 22, 2019

(54) MULTI-MODALITY CASE EXPLORER SYSTEM AND METHOD

(71) Applicant: Volcano Corporation, San Diego, CA (US)

(72) Inventors: Apollo Balignasay, Rancho Cordova, CA (US); Richard E. Mansker, Sacramento, CA (US); Asher Cohen, Sacramento, CA (US)

(73) Assignee: VOLCANO CORPORATION, San Diego, CA (US)

( * ) Notice: Subject to any disclaimer, the term of this patent is extended or adjusted under 35 U.S.C. 154(b) by 235 days.

(21) Appl. No.: 14/135,186

(22) Filed: Dec. 19, 2013

(65) Prior Publication Data
US 2014/0188503 A1 Jul. 3, 2014

Related U.S. Application Data

(60) Provisional application No. 61/746,897, filed on Dec. 28, 2012.

(51) Int. Cl.
G06F 19/00 (2018.01)
G16H 10/60 (2018.01)
G16H 15/00 (2018.01)

(52) U.S. Cl.
CPC ............ *G16H 10/60* (2018.01); *G16H 15/00* (2018.01)

(58) Field of Classification Search
CPC ................... G06Q 50/22; G06Q 50/24; G06F 19/322–327
USPC ........................................................ 705/2–3
See application file for complete search history.

(56) References Cited

U.S. PATENT DOCUMENTS

| 6,557,102 | B1 | 4/2003 | Wong | |
| 2002/0083075 | A1* | 6/2002 | Brummel | G06Q 50/22 |
| 2005/0223045 | A1 | 10/2005 | Funahashi | |
| 2006/0074711 | A1* | 4/2006 | Mahesh | G06F 19/321 |
| | | | | 705/2 |
| 2007/0269017 | A1 | 11/2007 | Umeki et al. | |

(Continued)

FOREIGN PATENT DOCUMENTS

| JP | 2002132557 A | 5/2002 |
| JP | 2007286945 A | 11/2007 |
| JP | 2008234309 A | 10/2008 |

(Continued)

OTHER PUBLICATIONS

Gjermundrod, Harald, et al. "Intensive care window: A multi-modal monitoring tool for intensive care research and practice." Twentieth IEEE International Symposium on Computer-Based Medical Systems (CBMS'07). IEEE, 2007.*

*Primary Examiner* — Mark Holcomb

(57) ABSTRACT

Generally, the present disclosure is directed to displaying patient medical data in a multi-modality medical processing system. The method and system described herein present medical data in multiple different modalities on a single user interface screen, allowing a practitioner viewing the user interface to manage all acquired data sets associated with a patient regardless of modality. As such, the amount of time a practitioner must spend reviewing patient medical data is reduced, leading to more efficient diagnosis and treatment. Further, multiple patient cases corresponding to different patients may be presented on a single user interface screen to simplify multi-patient case management.

22 Claims, 16 Drawing Sheets

(56) References Cited

U.S. PATENT DOCUMENTS

2011/0110496 A1* 5/2011 Foos .................... A61B 6/4405
378/98.5
2012/0041779 A1 2/2012 Arbash

FOREIGN PATENT DOCUMENTS

| JP | 2011048672 A | 3/2011 |
|----|--------------|--------|
| WO | 2008038614 A1 | 4/2008 |

* cited by examiner

MULTI-MODALITY CASE EXPLORER SYSTEM AND METHOD

CROSS-REFERENCE TO RELATED APPLICATIONS

The present application claims priority to and the benefit of U.S. Provisional Patent Application No. 61/746,897, filed Dec. 28, 2012, which is hereby incorporated by reference in its entirety.

TECHNICAL FIELD

Embodiments of the present disclosure relate generally to the field of medical devices and, more particularly, to a multi-modality case explorer system and method.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. Traditionally, when a patient undergoes multiple procedures associated with different modalities, it may be necessary to enter identifying information about the patient for each of the different modalities. In other words, the same patient information may have to be entered multiple times. Such duplication of effort may lead to clerical errors and wasted resources. Further, inconsistencies in patient diagnosis may be caused by each modality maintaining a separate patient record for the same patient.

Additionally, data associated with each medical modality is traditionally acquired and managed by distinct hardware or software systems. As a result, a practitioner may review a data set associated with a first medical modality on a different system than a data set associated with a second, different medical modality. Transitioning between systems to review data acquired from the same patient may lead to inefficient and inaccurate diagnoses. Further, archival mechanisms and archival storage locations may be different between different modality acquisition systems. For example, a patient's IVUS data may be archived in a different location and in a different format that the same patient's OCT data, making data retrieval inefficient and burdensome.

Further, when archived medical data is used for teaching and other non-diagnostic purposes, it is typical to remove any information that may identify the patient from which the data was acquired. Traditionally, removal of identifying information before archival is done by a technician who manually deletes patient data from selected fields. Anonymizing data in such a manner is often error prone and often does not result in all identifying information being removed.

Accordingly, while the existing case management systems and methods have been generally adequate for their intended purposes, they have not been entirely satisfactory in all respects.

SUMMARY

Generally, the present disclosure is directed to displaying patient medical data in a multi-modality medical processing system. The method and system described herein present medical data in multiple different modalities on a single user interface screen, allowing a practitioner viewing the user interface to manage all acquired data sets associated with a patient regardless of modality. As such, the amount of time a practitioner must spend reviewing patient medical data is reduced, leading to more efficient diagnosis and treatment. Further, multiple patient cases corresponding to different patients may be presented on a single user interface screen to simplify multi-patient case management.

In one exemplary aspect, the present disclosure is directed to a method of displaying multi-modality medical data with a multi-modality medical processing system. The method includes receiving first medical data acquired from a patient from a first medical instrument, the first medical data being associated with a first medical modality, storing the first medical data in a data repository, receiving second medical data about the patient from a second medical instrument, the second medical data being associated with a second medical modality different than the first medical modality, and storing the second medical data in the data repository. The method also includes displaying selectable representations of each of the first medical data and the second medical data on a user interface, receiving a user selection of the selectable representation of the first medical data, and displaying, in response to receiving the user selection, the first medical data in the user interface.

In another exemplary aspect, the present disclosure is directed to a multi-modality medical processing system. The system includes a data repository and a non-transitory, computer-readable storage medium that stores a plurality of instructions for execution by at least one computer processor. The instructions are for receiving first medical data acquired from a patient from a first medical instrument, the first medical data being associated with a first medical modality storing the first medical data in the data repository, receiving second medical data acquired from the patient from a second medical instrument, the second medical data being associated with a second medical modality different than the first medical modality, and storing the second medical data in the data repository. The instructions are also for displaying selectable representations of each of the first medical data and the second medical data on a user interface, receiving a user selection of the selectable representation of the first medical data, and displaying, in response to receiving the user selection, the first medical data in the user interface.

In yet another exemplary aspect, the present disclosure is directed to another method of displaying multi-modality medical data with a multi-modality medical processing system. The method includes maintaining a first patient case corresponding to a first patient, the first patient case including a first data set associated with a first medical modality and a second data set associated with a second medical modality different than the first modality and maintaining a second patient case corresponding to a second patient, the second patient case including medical data acquired from the second patient. The method also includes displaying selectable representations of each of the first patient case and the second patient case on a user interface, receiving a first user selection of the selectable representation of the first patient case, and displaying, in response to receiving the first user selection, selectable representations of each of the first data set and the second data set on the user interface. The method also includes receiving a second user selection of the selectable representation of the first data set and displaying, in response to receiving the second user selection, the first data set on the user interface.

DETAILED DESCRIPTION

Figure 1:
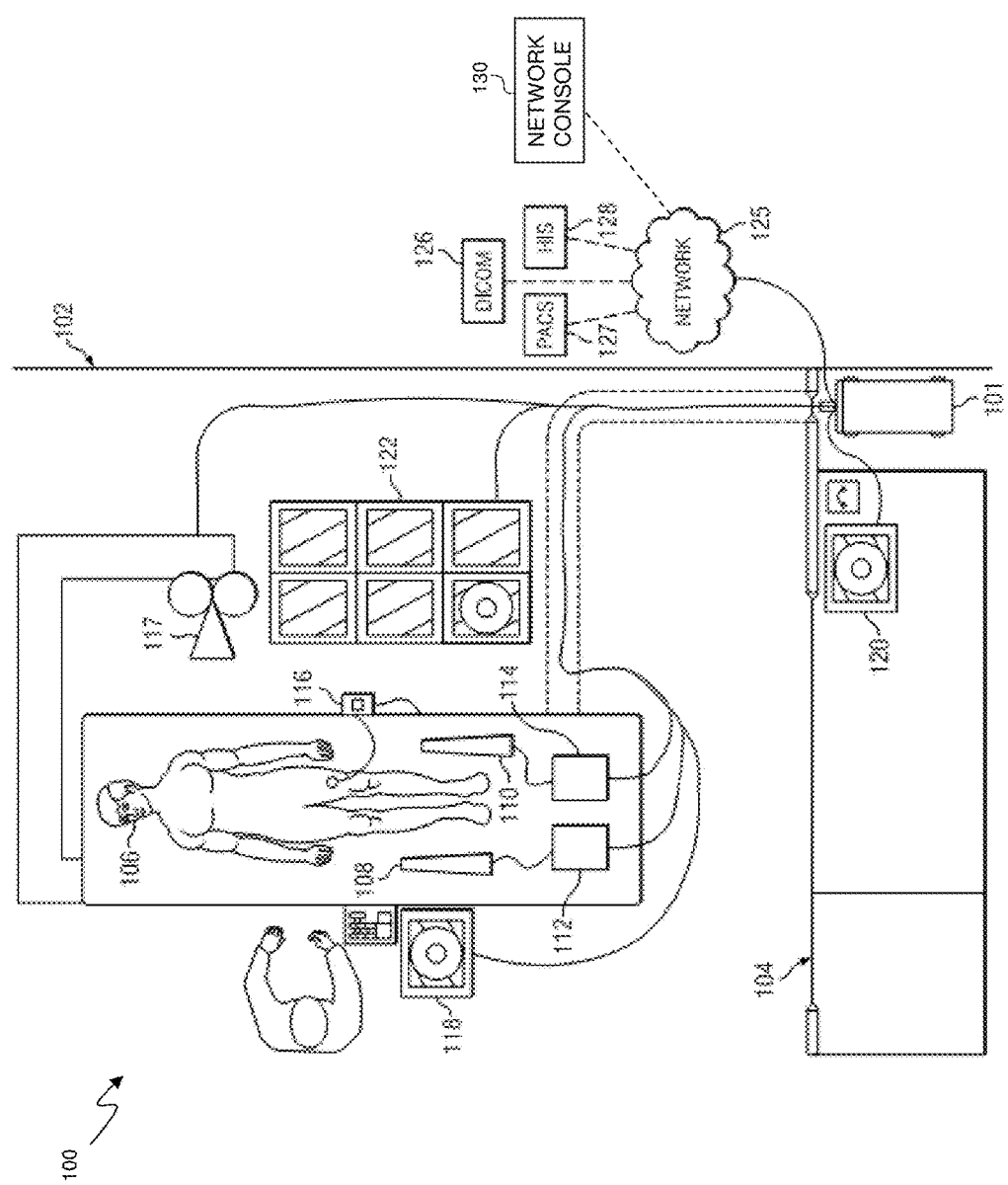
FIG. 1 is a schematic drawing depicting a medical system including a multi-modality processing system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information and coordinate treatment of various conditions. More specifically, in system 100, the multi-modality processing system 101 is an integrated device for the acquisition, control, interpretation, and display of multi-modality medical sensing data. In one embodiment, the processing system 101 is a computer system with the hardware and software to acquire, process, and display multi-modality medical data, but, in other embodiments, the processing system 101 may be any other type of computing system operable to process medical data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller. In that regard, in some particular instances the processing system 101 is programmed to execute steps associated with the data acquisition and analysis described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in a medical facility, or at an off-site location (i.e., in the cloud). The catheter lab 102 includes a sterile field generally encompassing a procedure area but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, an instantaneous wave-free ratio (iFR) determination, an x-ray angiography (XA) imaging, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

In the illustrated embodiment of FIG. 1, instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. The devices 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114 respectively couple the IVUS catheter 108 and OCT catheter 110 to the medical system 100. In particular, the IVUS PIM 112 and the OCT PIM 114 are operable to respectively receive medical sensing data collected from the patient 106 by the IVUS catheter 108 and OCT catheter 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system to the processing system 101 through an adapter device. Such an adaptor device may transform data from a proprietary third-party format into a format usable by the processing system 101. In some embodiments, the processing system 101 may be operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, the bedside controller 118 includes a user interface (UI) framework service through which workflows associated with multiple modalities may execute. Thus, the bedside controller 118 is capable displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality processing system 101 is communicatively coupled to a data network 125. In the illustrated embodiment, the data network 125 is a TCP/IP-based local area network (LAN), however, in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality processing system 101 via the network 125 to allow a doctor or other health professional to access the aspects of the medical system 100 remotely. For instance, a user of the network console 130 may access patient medical data such as diagnostic images collected by multi-modality processing system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
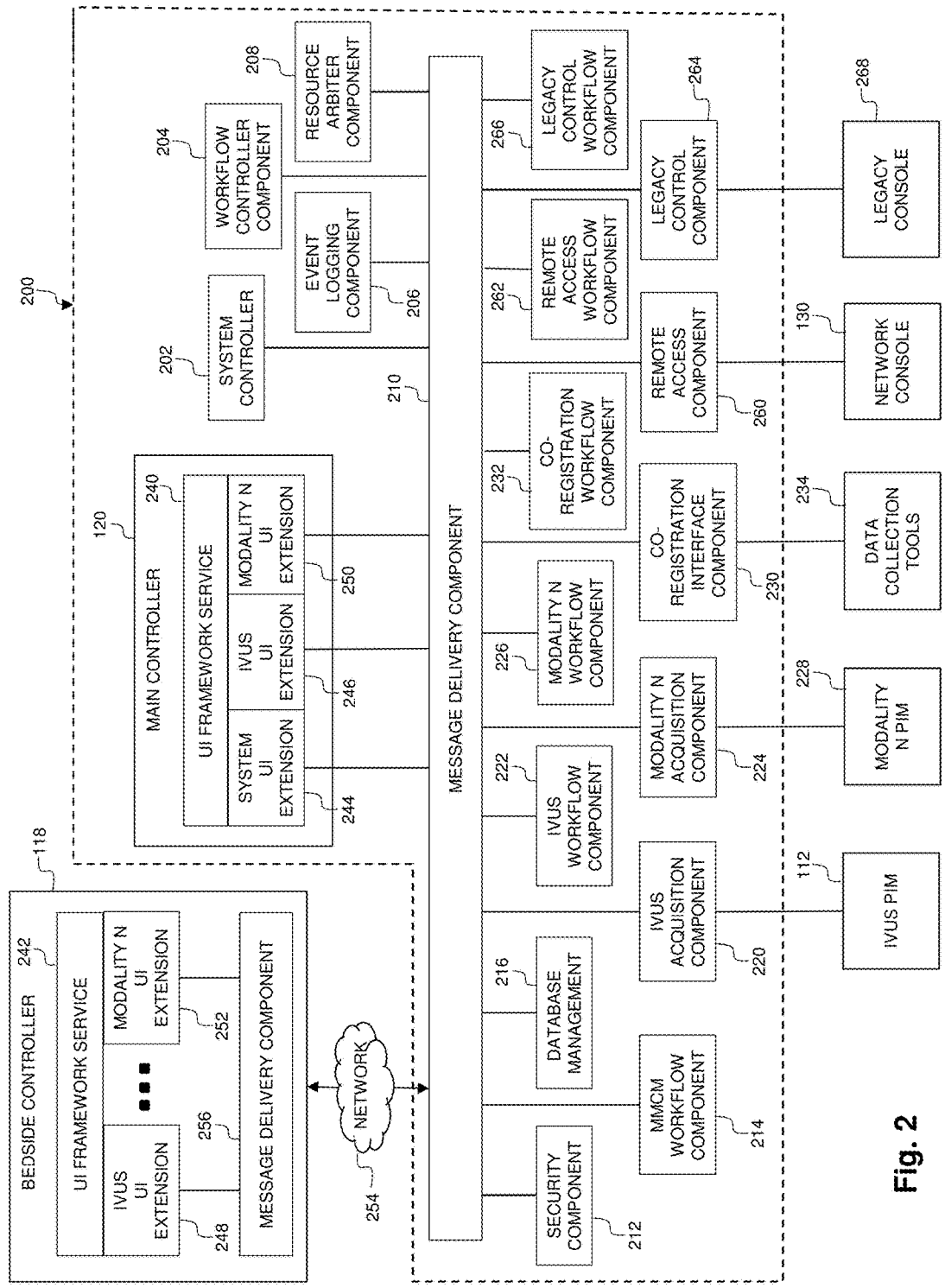
FIG. 2 is a functional block diagram of portions of the medical system, including a processing framework executing on an embodiment of the multi-modality processing system.

With reference now to FIG. 2, illustrated is a functional block diagram of portions of the medical system 100, including a processing framework 200 executing on an embodiment of the multi-modality processing system 101. The processing framework 200 includes various independent and dependent executable components that control the operation of the processing system 101, including the acquisition, processing, and display of multi-modality medical sensing data. In general, the processing framework 200 of processing system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the processing system 10. In other instances the processing framework 200 may be a combination of hardware and software modules executing within with the processing system 101.

Generally, in the embodiment shown in FIG. 2, processing framework 200 includes a plurality of components that are configured to receive medical sensing data from a plurality of medical sensing devices, process the data, and output the data as diagnostic images via the main controller 120, the bedside controller 118, or other graphical display device. The framework 200 includes several system-level components that manage the core system functions of the processing system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during multi-modality medical sensing workflows. The workflow controller component 204 may govern workflows executed by the processing framework 200 in various different manners.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. The resource arbiter component 208 may coordinate sharing of limited system resources in various manners such as through a lock system, a queue system, or a hierarchical collision management system.

In one embodiment, the system controller 202, workflow controller component 204, event logging component 206, and resource arbiter component 208 may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to dynamically alter the programmable logic within the FPGAs to implement various functionality needed at the time. As an aspect of this, the processing system 101 may include one or more unassigned FPGAs that may be allocated by the system controller during system startup. For instance, if upon startup of the processing system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality processing system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the processing system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 210 may be accessed by software and hardware modules in processing system 101 using Direct Memory Access (DMA).

The processing framework 202 further includes a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable perform additional and/or different database services such as data formatting services that prepare diagnostic data for database archival.

As mentioned above, the processing framework 200 of the multi-modality processing system 101 is operable to receive and process medical data associated with a plurality of modalities. In that regard, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the processing system 101 may be communicatively coupled to the OCT PIM 114, the ECG system 116, a fractional flow reserve (FFR) PIM, a FLIVUS PIM, and an ICE PIM. In other embodiments, additional and/or different medical sensing, treatment, or diagnostic devices may be coupled to the processing system 101 via additional and/or different data communication connections known in the art. In such a scenario, in addition to the IVUS acquisition module 220, the processing framework 200 may include an FFR acquisition component to receive FFR data from an FFR PIM, a FLIVUS acquisition component to receive FLIVUS data from a FLIVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the processing system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to processing system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1. In certain embodiments, the interface component 230 may be operable to standardize and/or transform incoming modality data such that it may be co-registered with other sensing data acquired by the processing system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1, a clinician utilizing the processing system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the processing system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the processing system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality processing system 101. For example, the framework 200 includes a remote access component 260 that communicatively couples the network console 130 (FIG. 1) to the processing framework 200. In one embodiment, the remote access component 260 is operable to export control functionality of the processing system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

Figure 3A:
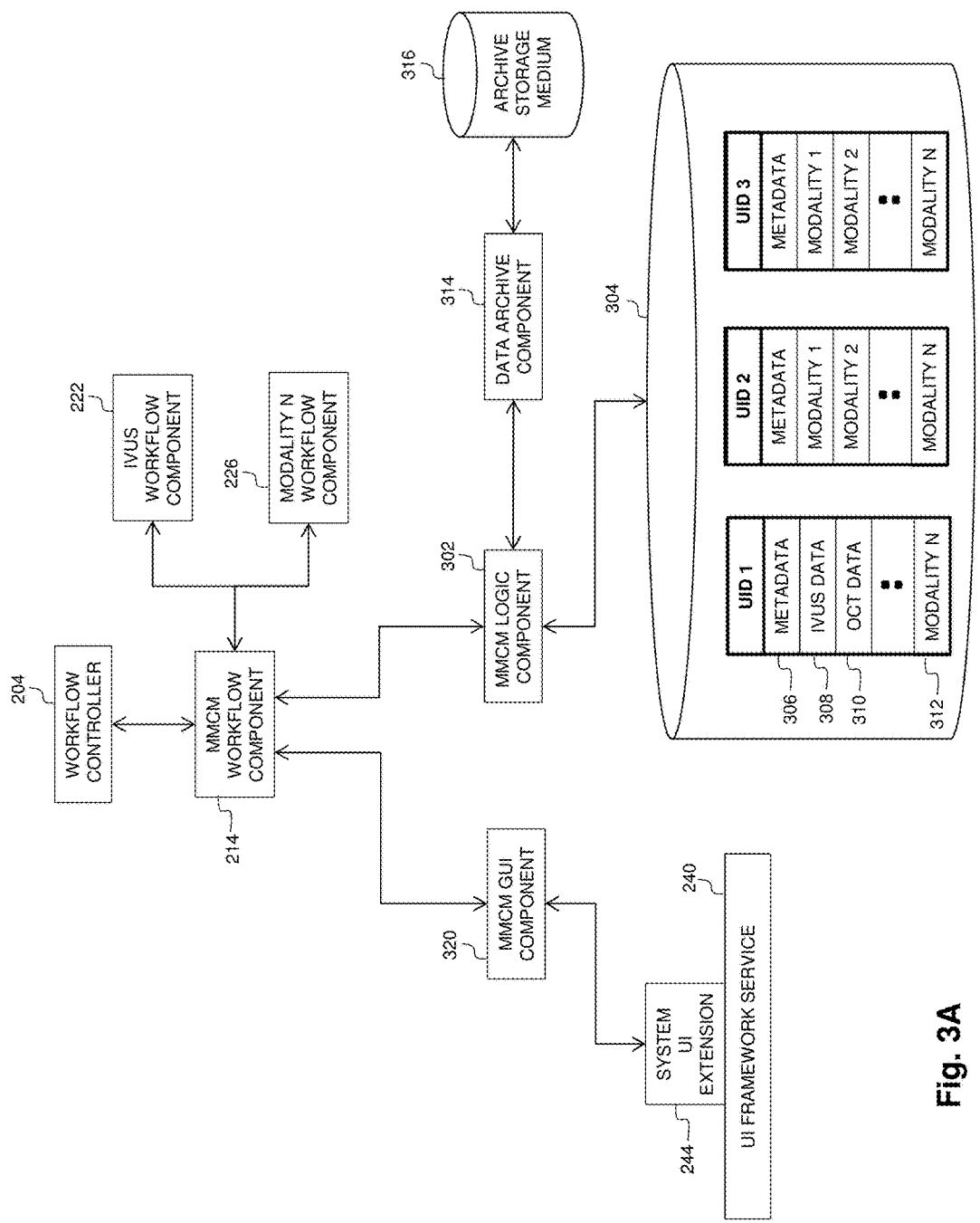
FIG. 3A is a functional block diagram of portions of the processing framework of FIG. 2, the portions being associated with multi-modality case management.

With reference now to FIG. 3A, illustrated is a functional block diagram of portions of the processing framework 200 associated with the multi-modality case management (MMCM) workflow component 214. As noted above, the MMCM workflow component 214 is configured to coordinate and consolidate patient medical data associated with a plurality of medical modalities into a unified patient record that may be more easily managed. In particular, in the illustrated embodiment, the MMCM workflow component 214 associates a unique identifier (UID) with every aspect of a patient case including both medical data acquired from medical instruments and metadata (non-acquired data) describing the patient, the acquired data, and the procedure. The UID may be a number, alphanumeric key, hexadecimal value, or any other item that may be used to uniquely identify a patient. The metadata associated with a UID may include identifying information about the patient (e.g., patient name, gender, date of birth, social security number, blood type, etc.), derived data associated with the acquired medical data (measurements, generated borders on intravascular images, etc.), annotations on images generated from the acquired medical data (vessel name, practitioner notes, internal structure identification, etc.), and information about the procedure performed on the patient (e.g., procedure time, procedure location, practitioner name, medical instruments utilized, etc.). Assigning a common unique identifier to both the patient metadata and acquired data creates a strong association required for efficient data retrieval and analysis (i.e., measurements must be associated with a single intravascular image; a vessel name annotation must be associated with all frames of a multi-frame image). Further, in the illustrated embodiment, a common unique identifier is assigned to all data acquired from a patient irrespective of the modality of the data. For example, a patient may typically undergo multiple different diagnostic procedures so that a practitioner may more fully assess the patient's condition. In that regard, data acquired during an IVUS procedure on the patient may be assigned the same UID as data acquired during an OCT procedure on the patient. In some instances the procedures may be performed during a single catheter lab session and in other instances they may be performed during multiple sessions separated by hours, days, months, or years. In any case, all diagnostic and/or treatment data acquired from the same patient is assigned the same unique identifier for improved patient diagnostics and, ultimately, treatment.

The MMCM workflow component 214 illustrated in FIG. 3A coordinates the assignment of a common UID to all metadata and acquired data related to a patient case. Specifically, the modality-specific workflow components—for example the IVUS workflow component 222 and modality N workflow component 226—utilize the MMCM workflow component 214 to store medical data acquired from a patient with medical instruments such as catheter-based transducers. In one embodiment, the MMCM workflow component 214 exposes a library of storage-related functions to the modality workflow components so that they may store and retrieve patient data from a designated storage medium. As such, storage of acquired data is handled in a uniform manner rather than each modality component implementing its own storage mechanisms including file management mechanisms and data formatting mechanisms, etc. As an aspect of this, when the MMCM workflow component 214 receives storage/retrieval requests from modality-specific components, it can coordinate a single set of patient metadata with medical data acquired from a patient across multiple different modalities.

The MMCM workflow component 214 includes a MMCM logic component 302 that implements the storage and retrieval functionality of the library called by the modality-specific components. In one embodiment, the MMCM logic component 302 may be implemented as a hierarchical state machine, but, in other embodiments, it may be implemented as an executable or another logic container. The MMCM logic component 302 generates unique identifiers and associates them with newly acquired data and metadata within a patient case. In one embodiment, a single patient case may be "open" at a time within the processing framework 200 and the MMCM logic component 302 ensures all data acquired or entered by a practitioner while the case is open is associated with the same study (case) UID. During a diagnostic procedure that acquires data from a patient, the MMCM logic component 302 assigns the current UID to the acquired data and stores it in a data repository 304. The data repository 304 may implement any type of logical data container such as a database and be stored on any type of storage medium such as a hard drive on the multi-modality processing system 101 or at a networked storage location. In one embodiment, the repository is an XML database that is accessed through a Shared Patient Information Management System (SPIMS). As illustrated in FIG. 3A, both a patient's metadata (e.g., identifying information, image annotation, etc) and acquired diagnostic data across modalities are stored in the repository 304 in association with the same UID. For example, as shown in FIG. 3A, UID 1 is associated with a patient case that includes metadata 306, IVUS data 308, OCT data 310, and modality N data 312. One of ordinary skill in the art would recognize that the organization of the data in the repository 304 is simply an example, all data associated with a patient case may be coordinated with a UID in numerous different manners, such as with a database table, data structure, hash table, stack, queue, linked list, etc. In one instance, all data associated with a medical modality is stored together in a logical data partition, but each data set within the group of modality data may be associated with a UID corresponding to the patient case to which it belongs. Further, the acquired patient data may be stored in the repository 304 in a number of different formats. For instance, it may be stored in "raw" form unchanged from the format generated by the acquiring medical instrument, or it may be stored in processed form—for example, as intravascular IVUS images. As discussed above, the data associated with a single UID may be collected over multiple clinical sessions, or maybe collected during a single session.

Figure 3B:
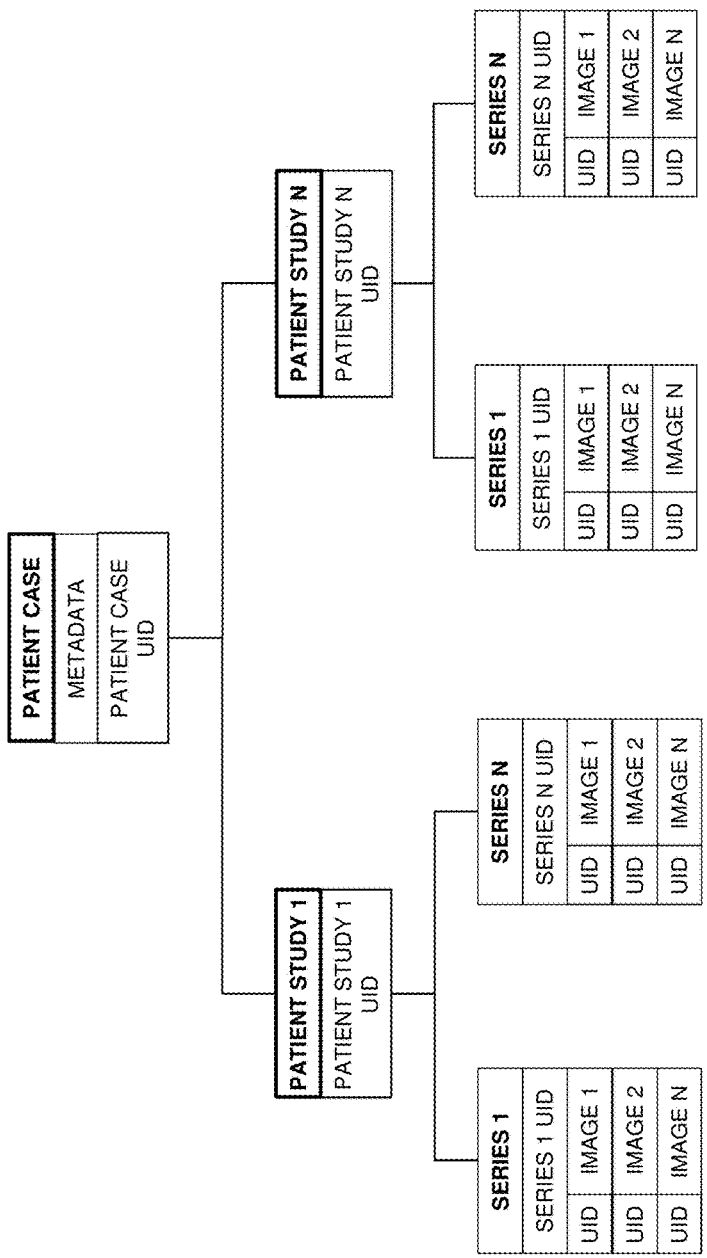
FIG. 3B illustrates an example patient case having unique identifiers at each hierarchical data level.

Additionally, in some embodiments, each hierarchical level of data within a patient record has its own unique identifier, such that there is a chain of unique identifiers that links all the patient data together. An example of a patient case having unique identifiers at each data level is illustrated in FIG. 3B. For example, a patient case that includes all data acquired or associated with a patient may have a global unique identifier, shown in FIG. 3B as the patient case UID. A patient case may include one or more patient studies, where each patient study includes all data collected during a catheter lab session. Each patient study may include its own unique identifier that is linked to the global patient case unique identifier. Further, each patient study, in turn, may include one or more data sets (or series) comprised of data in a specific medical modality. For instance, a patient study may include an IVUS series, an OCT series, and an FFR series that were all acquired during a single catheter lab session, where each series has its own unique identifier that is linked to the patient study unique identifier. Additionally, each data set or series may include one or more diagnostic images, where each image has its own unique identifier that is linked to the data set unique identifier. In this manner, the unique identifiers at each data level form a chain of ownership that links together patient metadata, patient studies, data sets (series), and individual images within a patient case.

Additionally, utilization of a unique identifiers for all data contained in a patient case simplifies data management within the multi-modality processing system 101. This scheme permits an entire patient case or each individual piece of data within a patient case to be identified and addressed. For example, upon review of patient data by a practitioner, the MMCM logic component 302 may retrieve all acquired diagnostic data, regardless of modality, with a single access of the repository using the UID associated with the patient case. Or, the MMCM logic component 302 may retrieve just a single image using the unique identifier associated with the image. Similarly, if patient data is no longer needed, all medical data associated with a patient, regardless of modality, may be deleted concurrently using the UID associated with the patient.

The MMCM logic component 302 may additionally interact with a data archive component 314 when a request to archive patient data is made by a practitioner. Specifically, as will be discussed in more detail in association with FIGS. 14-15, a practitioner may choose to archive all or parts of a patient case to a storage medium 316. The storage medium 316 may be a removable medium such as a writable Digital Versatile Disc (DVD), a writeable Blu-Ray Disc, a portable flash drive, or the storage medium 316 may be a fixed-typed storage such as a local hard drive, a DICOM server, or another networked archive repository. In one embodiment, upon an archive request, the MMCM logic component 302 may retrieve all data associated with a patient case from the repository 304 via the corresponding UID and then send the data to the data archive component 314 to be archived in association with the UID. In such a scenario, restoration of archived data may be accomplished through reference to the UID. Further, the data archive component 314 is configured, upon request, to anonymize data before it is archived. In embodiment, all identifying information about a patient may be removed from a patient case but the UID may remain associated with the case to facilitate efficient data management.

The MMCM workflow component 214 further includes a MMCM graphical user interface component 320 that drives the user interface components associated with managing a patient case. In particular, the MMCM GUI component 320 renders UI screens related to new patient case creation, collection of identifying information about a patient, management of previously-acquired modality data, and the archival of patient diagnostic data. As an aspect of this, the MMCM GUI component 320 is configured to interpret user commands entered in association with the user interface. The screens related to patient case management may be collectively referred to a case explorer. The user interface rendered by the MMCM GUI component 320 will be discussed in greater detail in association with FIGS. 4-13.

One of ordinary skill in the art would recognize that the aspects of the processing framework 200 associated with the MMCM workflow component 214 illustrated in FIG. 3A have been simplified and additional and/or different components may be executing within the framework to manage patient case data. For instance, the MMCM logic component 302 may utilize one or more database communication components to coordinate the transmission of data to and from the repository 304. Further, in some embodiments, each modality-specific workflow component may independently handle the storage of acquired diagnostic data. In such a scenario, each modality-specific workflow component may query the MMCM workflow component 214 for the UID corresponding to the currently open patient case and store the acquired diagnostic data in its dedicated storage container with the UID. Further, the MMCM workflow component 214 may store patient metadata in a separate MMCM storage container along with the corresponding UID.

Figure 4:
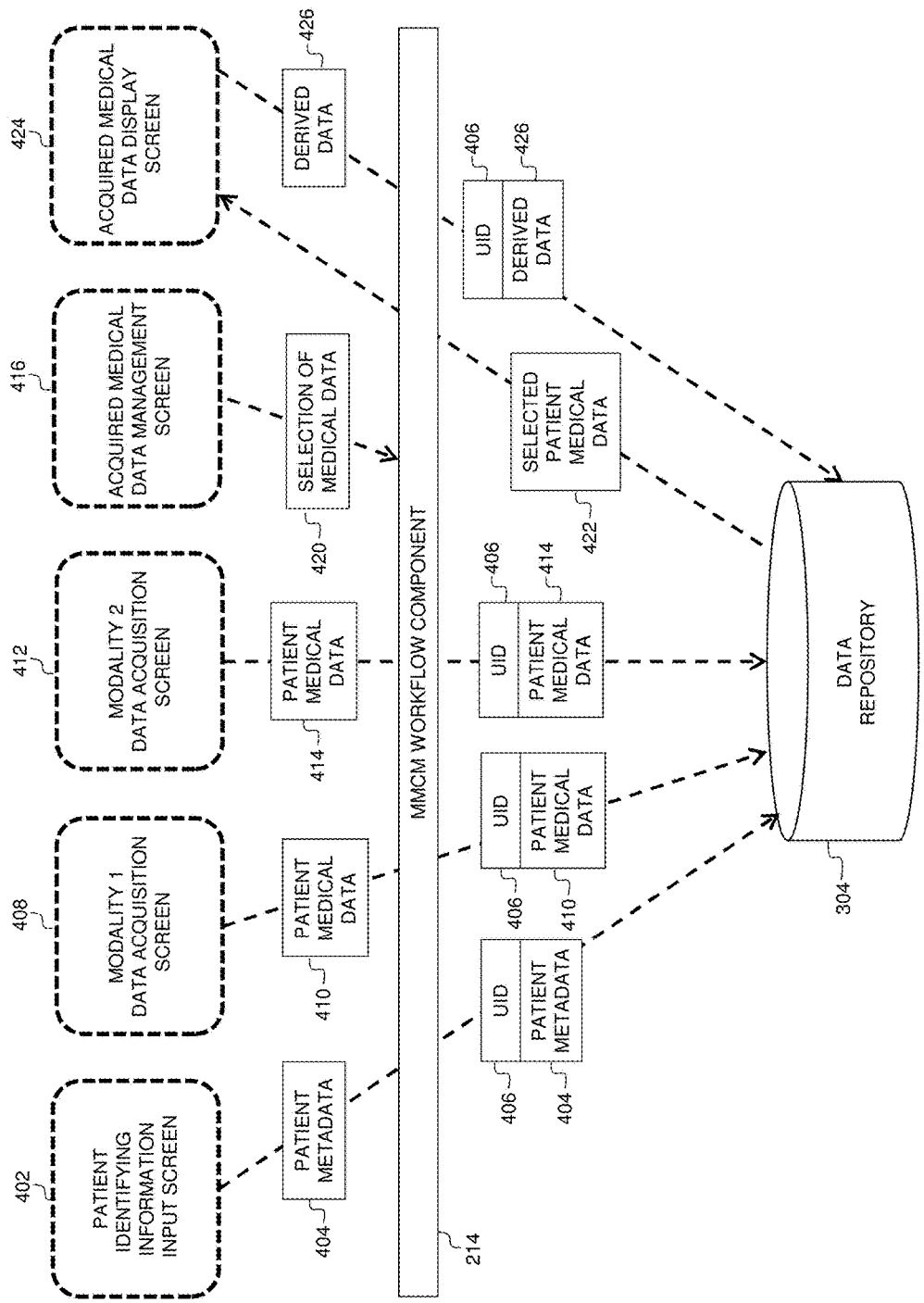
FIG. 4 is a simplified flow diagram of patient case management within the multi-modality processing system of FIG. 1 according to aspects of the present disclosure.
Figure 5:
FIGS. 5-13 are various example screens of a case management user interface rendered by the multi-modality processing system of FIG. 1.
Figure 6:
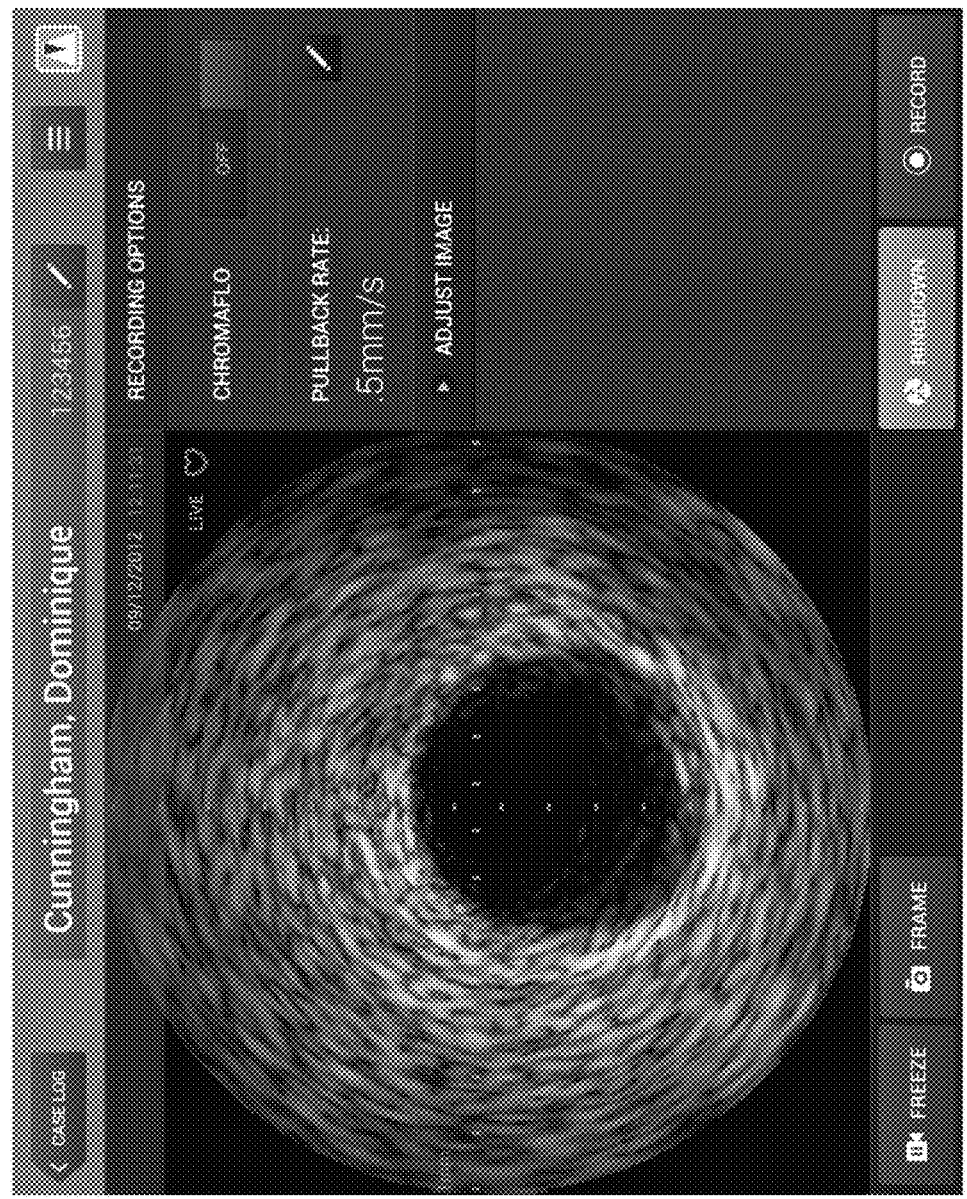
Figure 7:
Figure 8:
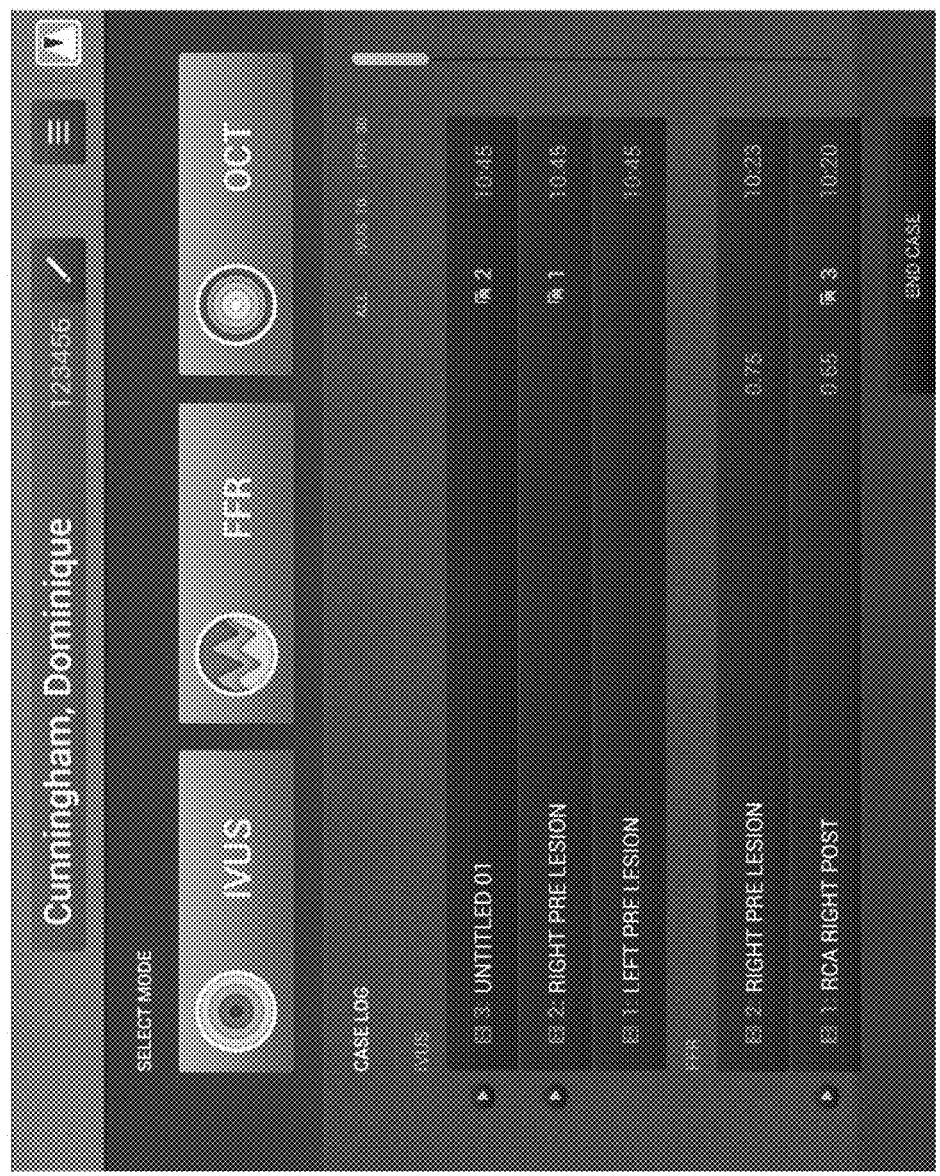

With reference now to FIG. 4, illustrated is a simplified flow diagram of patient case management within the multi-modality processing system 101. As discussed above, the MMCM workflow component 214 coordinates management of acquired and non-acquired patient data within the multi-modality processing system 101. The MMCM workflow controller 214 controls both the front-end user interface and the back-end data storage. The front-end user interface includes numerous screens to efficiently guide a practitioner though a patient case workflow. First, an identifying information input screen 402 allows a practitioner to initially enter identifying information about a new patient into the multi-modality processing system 101. An example identifying information input screen 402 is shown in detail in FIG. 5. The screen 402 permits entry of patient metadata including last name, middle name, first name, date of birth, gender, and UID. The UID may be entered by a practitioner or generated automatically by the MMCM workflow component. Further, the identifying information input screen 402 may be used to edit previously-stored patient information. By virtue of using a common unique identifier for all acquired patient data, regardless of modality, a practitioner need only enter the patient identifying information once when a patient case is initialized. In this manner, data entry errors are reduced and patient identifying information is ensured to be linked to the correct acquired diagnostic data. In alternative embodiments, patient identifying information may be retrieved from an external patient data repository such as a Hospital Information System (HIS). In such a case, the identifying information input screen 402 may prompt a practitioner for network connection information for the external data repository so that the patient metadata may be retrieved.

With reference back to FIG. 4, after a practitioner has entered patient metadata 404 into the screen 402, a patient case is initialized and the metadata 404 is passed to the MMCM workflow component 214 where the metadata is associated with a UID 406. The UID 406 may be the UID entered in the screen 402 or it may be a UID generated by the MMCM workflow component. After the patient metadata 404 has been associated with the UID 406, the MMCM workflow component 214 stores the metadata in the data repository 304. Upon opening a patient case by entering identifying information about the patient, a practitioner may perform one or more diagnostic and/or treatment procedures on the patient. A modality data acquisition screen 408 facilitates the acquisition of diagnostic data received from a medical instrument internal or external to the patient. An example modality data acquisition screen 408 is shown in detail in FIG. 6. The example screen 408 illustrates an IVUS acquisition workflow. An image of the patient's vessel as generated from data captured by an IVUS transducer is displayed to allow the practitioner to guide the delivery catheter through the patient. As discussed in association with FIG. 2, each modality may have a user interface extension that renders the screens needed to perform the diagnostic procedure associated with the particular modality. The screens associated with data management rendered by the MMCM workflow component 214 and the screens associated with data acquisition rendered by each modality extension are integrated into a seamlessly user interface by the system UI extension 244 (FIG. 2). With reference back to FIG. 4, patient medical data 410 associated with the first modality captured via the modality data acquisition screen 408 is transmitted to the MMCM workflow component 214 where it is associated with the UID 406 corresponding to the open patient case and then stored in the data repository 304. As such, the patient metadata 404 and patient medical data 406 are both stored in the data repository 304 in association with the UID 406. In one embodiment, the medical data 410 may be stored in the data repository 304 in the form received from the medical instrument, but, in another embodiment, the medical data may be stored as processed data, such as IVUS or OCT images.

In the example workflow of FIG. 4, a second data acquisition procedure is performed on the patient. The medical modality associated with the second data acquisition is different than the medical modality associated with the first data acquisition. The second data acquisition may be performed during the same catheter lab procedure as the first data acquisition or may be performed during a later procedure. The unique identifier methodology disclosed herein ensures that data collected during each acquisition is registered with the same patient, regardless of when the acquisitions occur. A second modality data acquisition screen 412 is presented to a practitioner to guide the second acquisition workflow. An example modality data acquisition screen 412 is shown in detail in FIG. 7. The example screen 412 illustrates an FFR diagnostic procedure. The screen 412 presents a practitioner with data representative of the flow of blood through a patient's vessel as acquired by a sensor disposed in the vessel. With reference back to FIG. 4, patient medical data 414 captured in association with the second data acquisition screen 412 is passed to the MMCM workflow component 214 where the same UID 406 is associated with the data and the data is stored in the data repository 304.

After diagnostic data associated with one or more modalities has been acquired from a patient, an acquired data management screen 416 allows a practitioner to review and manage the acquired data sets. An example acquired data management screen 416 is shown in detail in FIG. 8. The screen 416 includes a case log that displays a selectable representation of every acquisition procedure performed on a patient, regardless of modality. In other words, each of the data sets displayed in the case log are stored in the data repository 304 under the same UID that corresponds to the patient case. For instance, the example screen 416 includes both IVUS data sets and FFR data sets that were acquired from the same patient. The selectable representations displayed on the screen 416 may correspond to data sets acquired over a period of hours, days, weeks, or years, or they may correspond to distinct data sets acquired within the same procedure.

Figure 9:
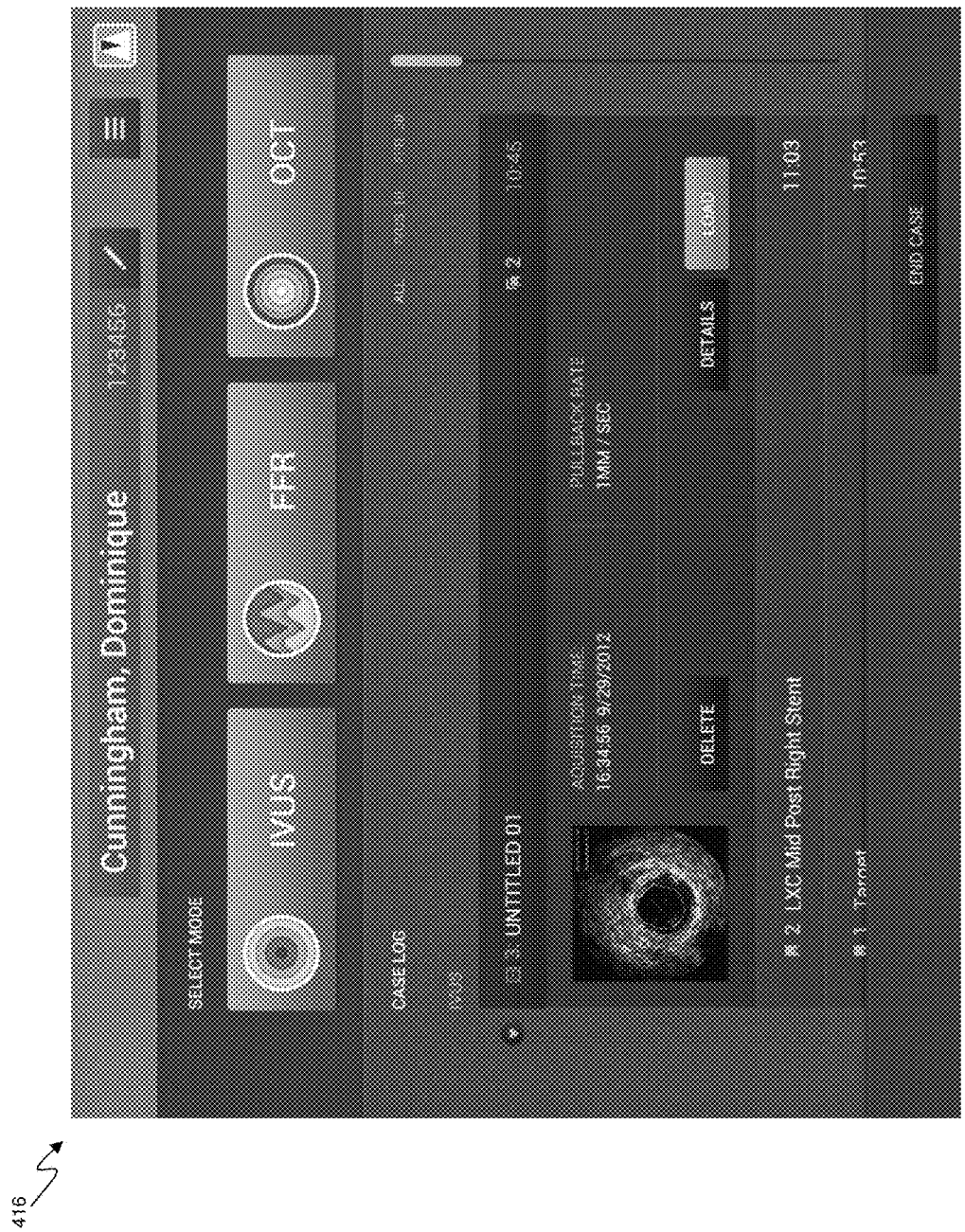

In one embodiment, to render the screen 416, the MMCM GUI component 320 queries the data repository 304 for a list of all acquisition data sets associated with the UID corresponding to the open patient case. In the example screen 416, all the data sets are associated with the unique identifier 123456, and the selectable representations are organized by modality type. Further, in the illustrated embodiment, each selectable representation of a data set displays the title of the data set, whether the data sets includes any bookmarks highlighting important patient features, and the date and time the data set was acquired. In other embodiments, additional information may be displayed in association with each selectable representation of a data set. Additionally, in some instances, the display order of the selectable representations in the case log may be altered based on various features of the data sets such as acquisition time. As will be described below, selecting a selectable representation on the screen 416 will cause the user interface to display the data and/or images contained in the selected data set. However, in some embodiment, selecting a selectable representation on the screen 416 causes the UI to display additional information about the selected data set within the screen 416, for example in a drop-down preview pane. For example, FIG. 9 illustrates a scenario where a practitioner has selected the data set titled "UNTITLED 01". Additional information about the data set including acquisition time, pull back rate, and the labels of the bookmarks within the data set are displayed beneath the selectable representation of the data set. Further, as shown in the illustrated embodiment, a preview of the image data contained within the data set may be additionally displayed. Within the drop-down preview pane, buttons to delete the data set, load the data set, and display additional details about the data set are selectable by a practitioner. Additionally, in some embodiments, the screen 416 may allow a practitioner to select more than one selectable representation of a data set for comparison purposes. Accordingly, a practitioner viewing the acquired data management screen 416 may easily view and manage all acquired data sets associated with a patient regardless of modality. As such, the amount of time a practitioner must spend reviewing patient medical data is reduced, leading to more efficient diagnosis and treatment.

Figure 10:
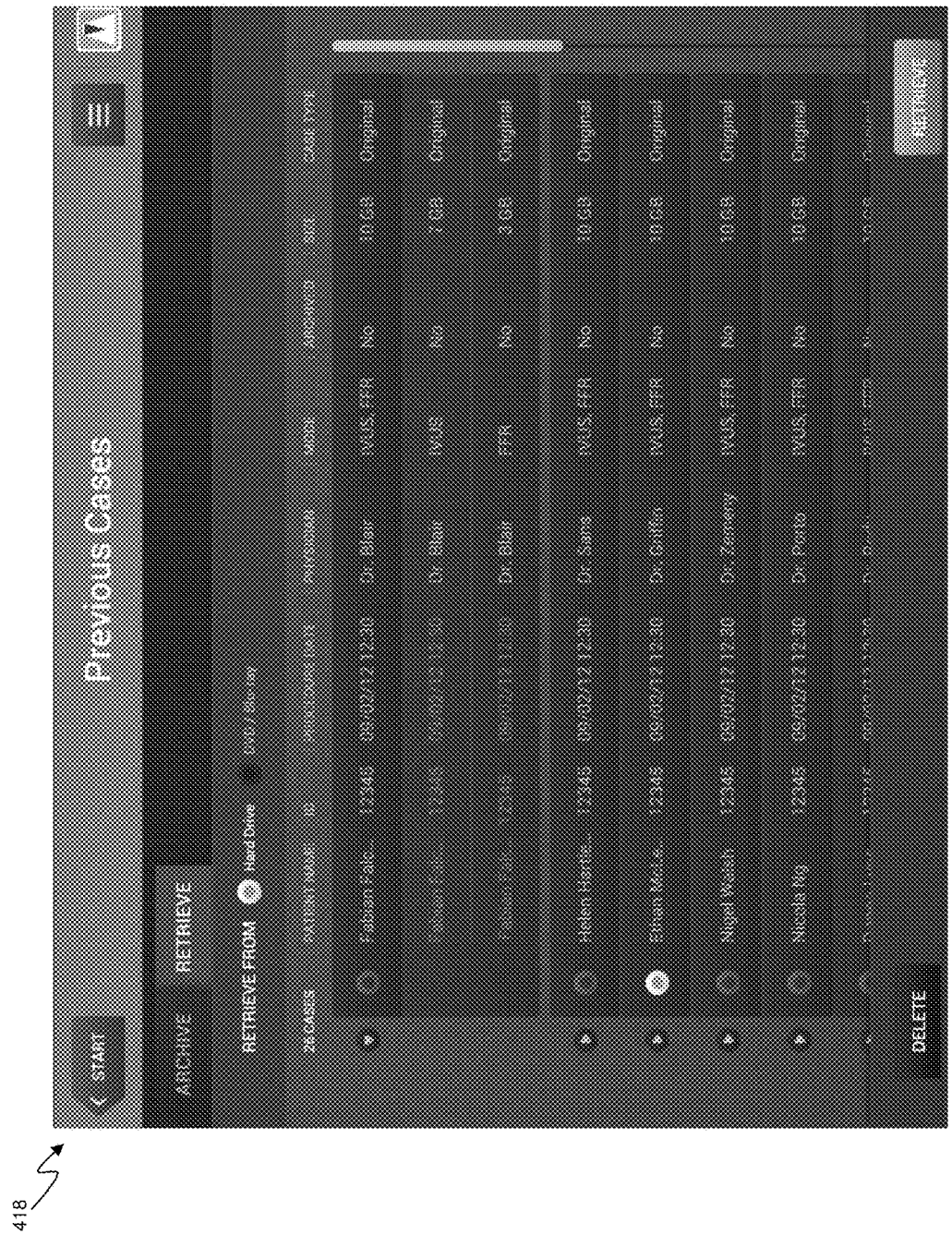

With reference now to FIG. 10, illustrated is a multi-patient acquired data management screen 418. The data management screen 418 is similar to the data management screen 416 but it is configured to display selectable representations of data sets associated with a plurality of patient cases. Each selectable representation of a patient case includes information about the patient case such as patient name, the unique identifier (UID), procedure date, physician, modality/mode, whether the data set is archived, the size of the data set, and the case type. In other embodiments, each selectable representation of a patient case may include different and/or additional information such as patient date of birth, patient gender, procedure location, etc. The display order of the patient cases listed on the data management screen 418 may be arranged by one or more of the information categories associated with each patient case. Further, in some embodiments, and as shown in FIG. 10, when a practitioner selects a toggle element associated with a selectable representation of a patient case, the individual data sets comprising the selected patient case are displayed. All acquired data sets associated with a patient case, regardless of medical modality, are displayed below the selectable representation. In the example of screen 418, the first patient case has been selected and data sets associated with an IVUS procedure and an FFR procedure are displayed. Additionally, the multi-patient acquired data management screen 418 is configured to allow a practitioner to retrieve and open a patient case by selecting one of the displayed selectable representations. When a selectable representation of a patient case is selected on the screen 418, the MMCM GUI component 320 queries the data repository 304 using the associated UID, and the data sets associated with the patient are retrieved. In some embodiments, a selected patient case may be retrieved from a local or network-based hard drive, but, in other embodiments, the selected patient case may be retrieved from a removable medium such as a DVD, Blu-ray disc, or flash-based drive. Accordingly, a practitioner viewing the multi-patient acquired data management screen 418 may easily view and manage all patient cases, including all acquired data sets contained in the patient cases regardless of modality. As such, a practitioner may efficiently identify and compare relevant patient cases, thus facilitating efficient diagnosis and treatment.

Figure 11:
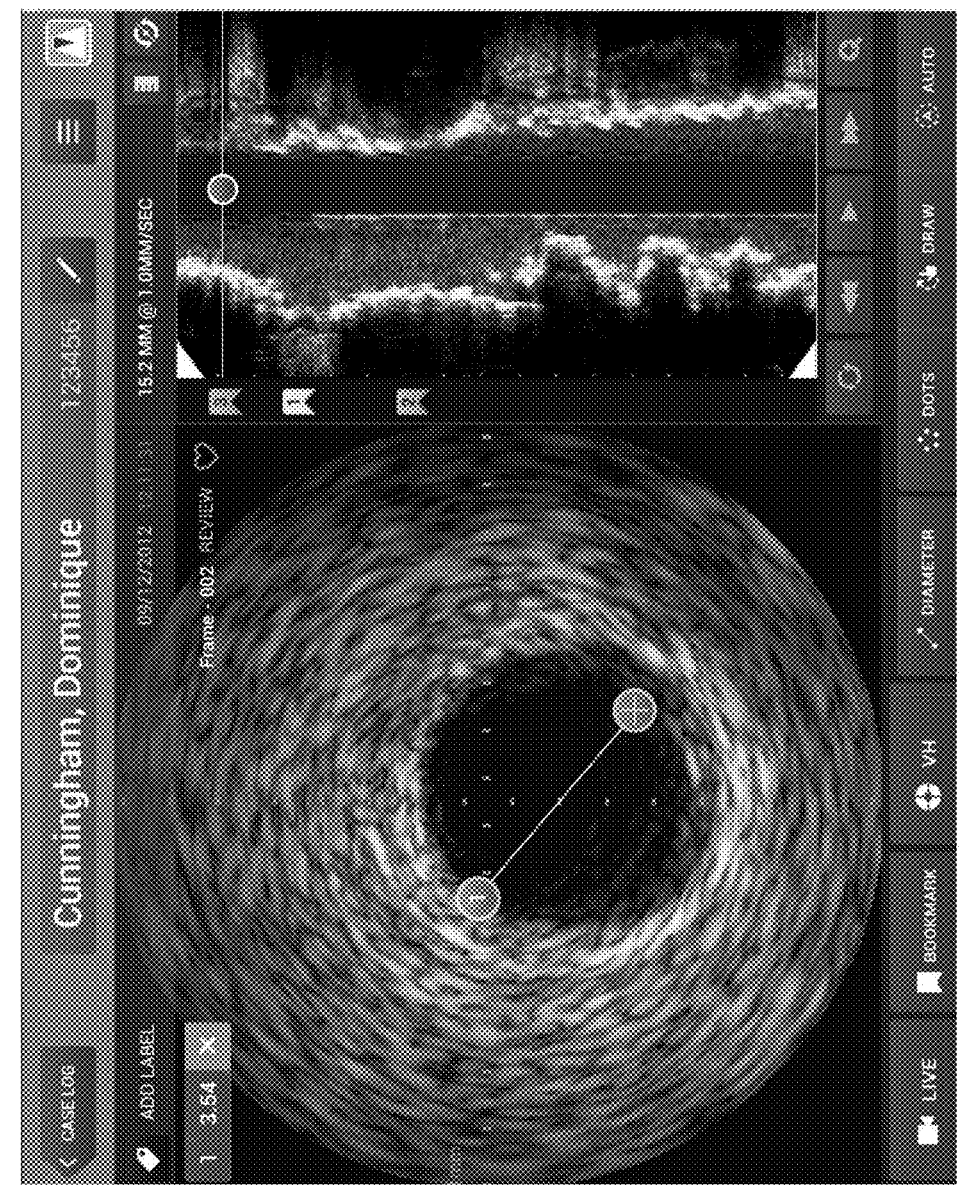

With reference now back to FIG. 4, a practitioner viewing the acquired data management screen 416 may select a particular data set to view in more detail, as described above. An identification of the selected medical data 420 is transmitted to the MMCM workflow component 214 so that the selected medical data may be retrieved from the data repository 304. Specifically, the MMCM workflow component 214 queries the data repository 304 using at least the UID of the selected medical data. As shown in the illustrated embodiment of FIG. 4, once the selected patient medical data 422 is retrieved from the data repository 304, it is displayed to the requesting practitioner via an acquired medical data display screen 424. In that regard, an example acquired medical data display screen 424 is illustrated in FIG. 11. The example display screen 424 shows an image data set captured during an IVUS procedure. In reviewing the IVUS images, a practitioner may make measurements and add labels and other annotations on the IVUS images in the data set. In that regard, methods and systems for enhanced measurement, manipulation, navigation, display, and annotation of multi-modality medical images are disclosed in U.S. Provisional Patent Application No. 61/746,012, filed Dec. 26, 2012, and entitled "DATA LABELING AND INDEXING IN A MULTI-MODALITY MEDICAL IMAGING SYSTEM,", U.S. Provisional Patent Application No. 61/746,010, filed DEC. 26, 2012, and entitled "MEASUREMENT AND ENHANCEMENT IN A MULTI-MODALITY MEDICAL IMAGING SYSTEM," U.S. Provisional Patent Application No. 61/745,999, filed Dec. 26, 2012,and entitled "GESTURE-BASED INTERFACE FOR A MULTI-MODALITY MEDICAL IMAGING SYSTEM," and U.S. Provisional Patent Application No. 61/745,986, filed Dec. 26, 2012,and entitled "MEASUREMENT NAVIGATION IN A MULTI-MODALITY MEDICAL IMAGING SYSTEM," all of which are hereby incorporated by reference in their entirety.

Figure 12:
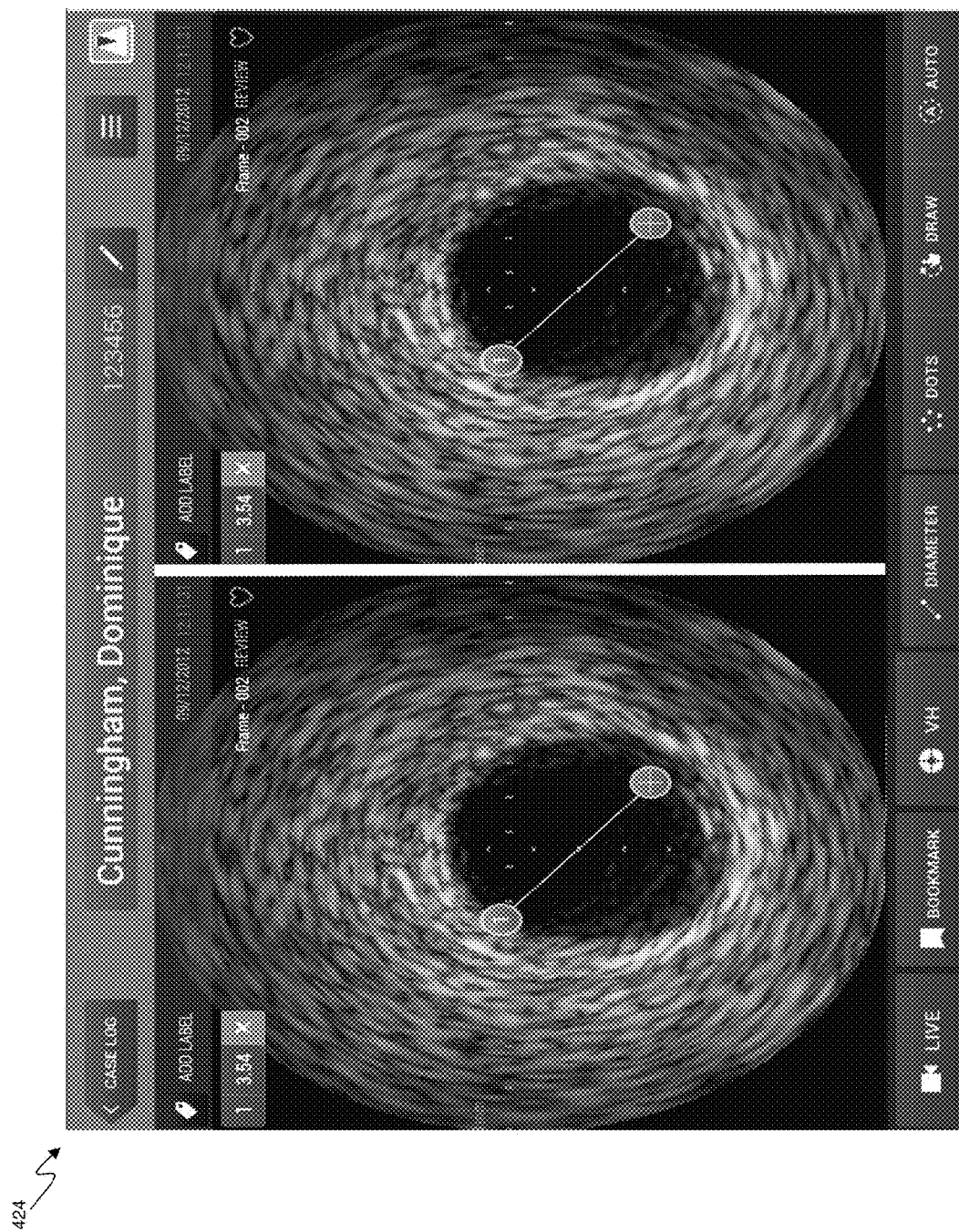
Figure 13:
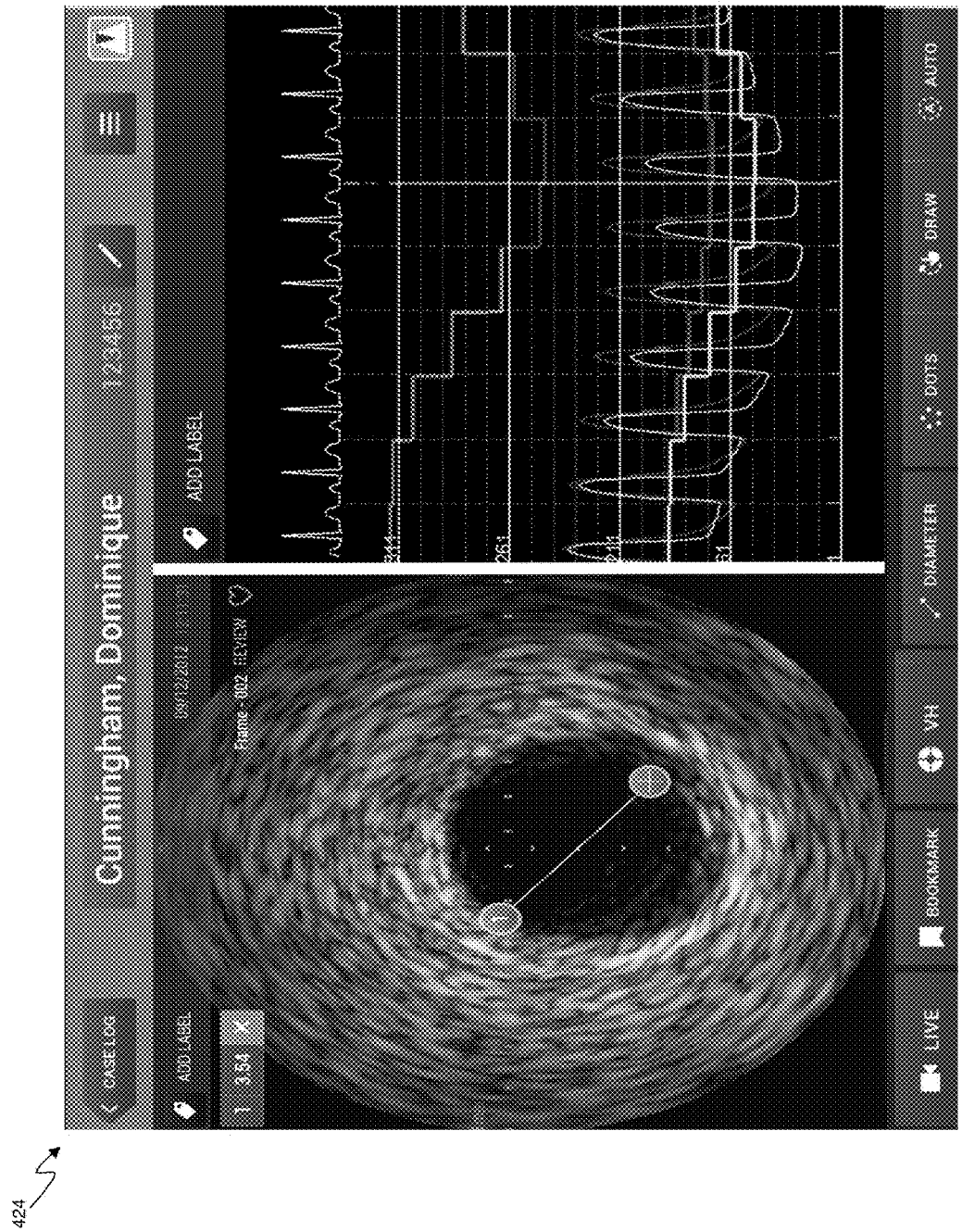

As discussed above, in some embodiments, the acquired data management screen 416 may allow a practitioner to select more than one selectable representation of a data set for comparison purposes. In such a scenario, the MMCM workflow component 214 may retrieve each of the requested data sets for simultaneous display on the acquired medical data display screen 424. FIG. 12 illustrates another example of the acquired medical data display screen 424 that shows two IVUS images side by side. The two IVUS images may be from data sets acquired during two different IVUS procedures performed on a patient. The side by side comparison of patient images acquired at different times, allows a practitioner to efficiently determine any changes in a patient's condition over time. Additionally, FIG. 13 is another example acquired medical data display screen 424 showing data associated with different modalities displayed side by side. Specifically, an IVUS image acquired from a patient is shown concurrently with FFR data collected from the same patient. The IVUS data and the FFR data may have been collected during the same catheter lab procedure or during different catheter lab procedures. The MMCM workflow component 214 may include synchronization components to spatially or temporally synchronizing the multi-modality data displayed in the screen 424. One of ordinary skill in the art would recognize that the screen 424 in FIG. 13 is just an example and that data in different modalities may be displayed side by side for comparison purposes. For example, an OCT image may be displayed adjacent an ICE image, or, in some instances, data acquired outside of (but streamed to) the multi-modality processing system 101, such as x-ray angiography (XA) data, may be displayed adjacent data acquired by the processing system itself, such as IVUS or OCT data.

Referring back to FIG. 4, any measurements, annotations, notes, or other derived data 426 created during a review of acquired data via screen 424 are transmitted to the MMCM workflow component 214. The MMCM workflow component 214 associates the UID 406 corresponding to the open patient case with the derived data 426 and stores the derived data 426 in the data repository 304. In this manner, any annotations, measurements, etc. are closely associated with their corresponding acquired data to facilitate efficient retrieval and subsequent review.

One of ordinary skill in the art would recognize that the system and method of patient case management described in association with FIGS. 4-13 is simply an example embodiment, and in alternative embodiments, additional and/or different steps may be performed and additional and/or different screens may be rendered as part of the user interface. For example, in one embodiment, each modality workflow component, rather than the MMCM workflow component, may handle the writing and retrieving of data associated with that modality. In such an embodiment, the independent modality workflow components may query the MMCM workflow component for the UID corresponding to the currently open patient case before storing any new acquired data. Further, the screens 402, 408, 412, 416, and 424 are simply examples and such screens may include different and/or additional features and user options to further facilitate patient case management within the multi-modality processing system 101.

Figure 14:
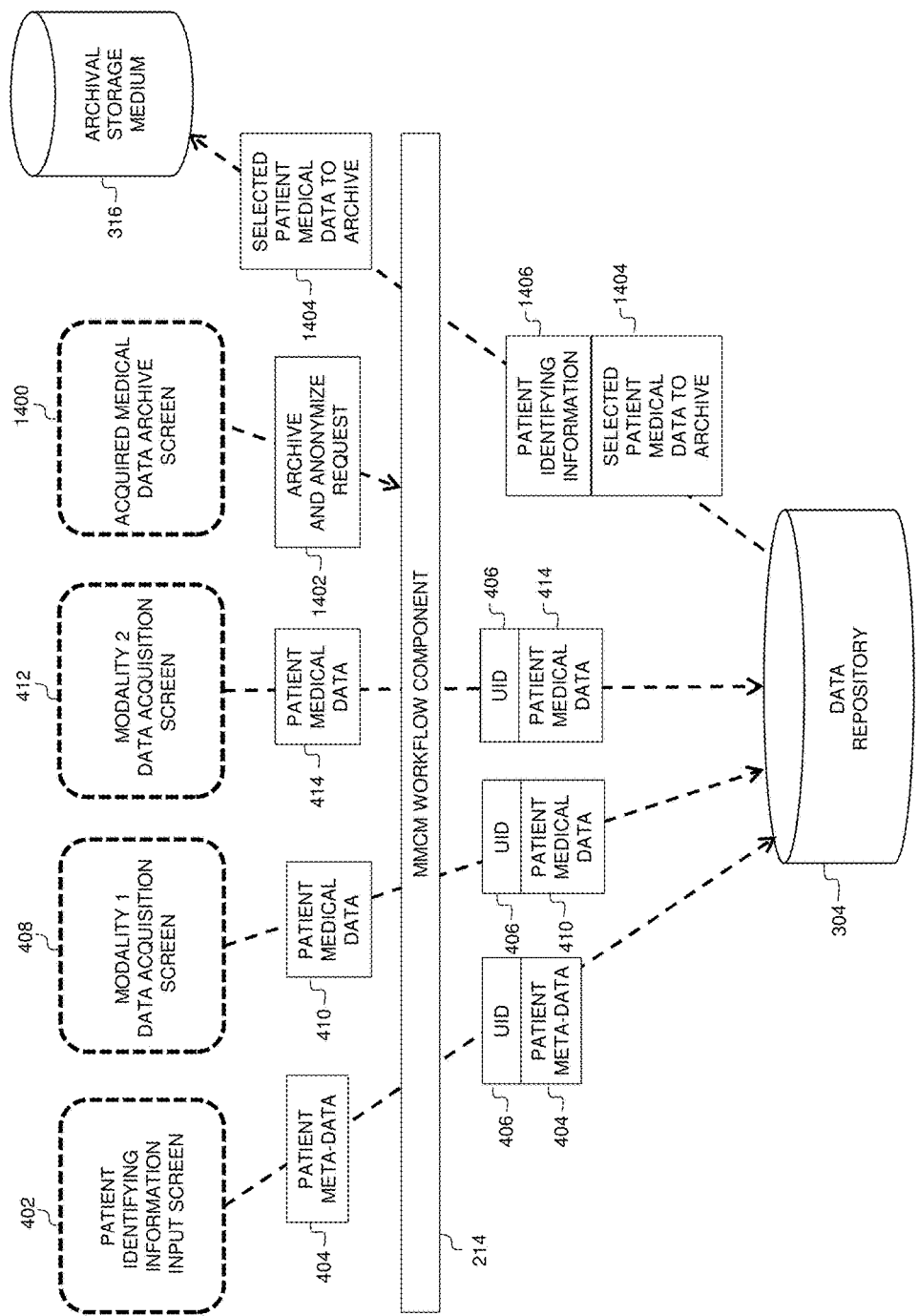
FIG. 14 is a simplified flow diagram showing archiving and anonymizing patient medical data within the multi-modality processing system of FIG. 1.

With reference now to FIG. 14, illustrated is flow diagram showing a different aspect of patient case management within the multi-modality processing system 101. Specifically, FIG. 14 shows systems and methods of archiving and anonymizing patient medical data. Portions of FIG. 14 similar to portions of FIG. 4 and have been labeled similarly for the sake of clarity.

After medical data associated with one or more modalities has been acquired from a patient and stored in the data repository 304, a practitioner has the option to archive the data to an archival storage medium, as discussed above in association with FIG. 3A. Generally, archiving acquired medical data includes moving the medical data to a storage location outside of the medical processing system through which the medical data was acquired. In one instance, acquired medical data may be transferred to a removable storage medium such as a writable optical disc or a portable flash-based container. In another instance, acquired medical data may be transferred to a remote, data repository such as DICOM over a network connection.

To facilitate archival of multi-modality patient records, the MMCM GUI component renders an acquired medical data archive screen 1400. An example acquired medical data archive screen 1400 is shown in detail in FIG. 15. The example archive screen 1400 displays a list of selectable representations of patient cases available for archival. Each selectable representation of a patient case includes information about the patient case such as patient name, the unique identifier (UID), procedure date, physician, modality/mode, whether the data set already archived, the size of the data set, and the case type. In some instances, the UID displayed in association with each patient case may be an identifier assigned by the clinic hospital treating the patient and may not be universally unique like a social security number. In other embodiments, each selectable representation of a patient case may include different and/or additional information such as patient date of birth, patient gender, procedure location, etc. The display order of the patient cases listed on the archive screen 1400 may be arranged one or more of the information categories associated with each patient case. Each representation of a patient case is selectable—for example, via a checkbox. Actuating a drop-down toggle associated with one of the patient cases further displays the modality data sets that comprise the patient case. For example, the first patient case displayed on screen 1400 includes a data set generated during an IVUS procedure and a data set generated during an FFR procedure. These data sets are displayed as representations that are independently selectable—for example, by selecting a checkbox to the left of the data set representation. In other embodiments, a different manner of selecting data sets may be implemented. Although not shown in example screen 1400, in further embodiments, each image-based data set within a patient case (i.e., an IVUS data set) may be expanded so as to display the individual images that comprise the data set. In such an embodiment, each image may be individually selectable—for example via a checkbox.

After a practitioner has reviewed the list of patient cases available for archive on the screen 1400, the practitioner may select one or more patient cases, data sets, or images for archival. In the illustrated embodiment, the practitioner would place checkmarks besides each item to be archived, and then actuate an archive button. Notably, the archival system of the present disclosure is configured to archive at the patient case level, at the data set level, and at the image level. That is, a practitioner may (1) selectively determine which patient case or plurality of patient cases to archive, (2) selectively determine which data set or plurality of data sets within a patient case to archive, and (3) selectively determine which image or plurality of images within a data set to archive. In some instances, any permutation of patient case, data set, or image may be archived together. As such, a single archive action may archive multiple patient cases corresponding to multiple patients concurrently. Also, an archived patient case may contain data sets associated with different medical modalities, and may also contain multi-modality data sets acquired during a single catheter lab procedure or acquired during different catheter lab procedures performed at different times.

As discussed in association with FIG. 3A, a patient case may be archived in association with its corresponding UID for efficient storage management and retrieval. In some embodiments, utilization of the UID allows an archived patient case to be updated with "new" patient data acquired after the initial archival action. In more detail, after a patient case has been archived, the screen 1400 will indicate as much in the "ARCHIVED" information column. When a new data set is acquired that is associated with a previously-archived patient case, the screen 1400 will indicate that the new data set is not archived. A practitioner may individually select the un-archived data set and actuate the archive button. In response, the archival system (implemented by the data archive component 314 in FIG. 3A or by the MMCM workflow component 214) locates the archived patient case via the associated UID, opens it, and inserts the new data set. In other embodiments, updating an archived patient case may be performed in a different manner such as by retrieving the data in the archived patient case, adding the new data set, and creating a new archive with the updated patient case. Further, in other embodiments, the MMCM workflow component prohibits data from being added to previously-archived cases to prevent data tampering.

Figure 15:
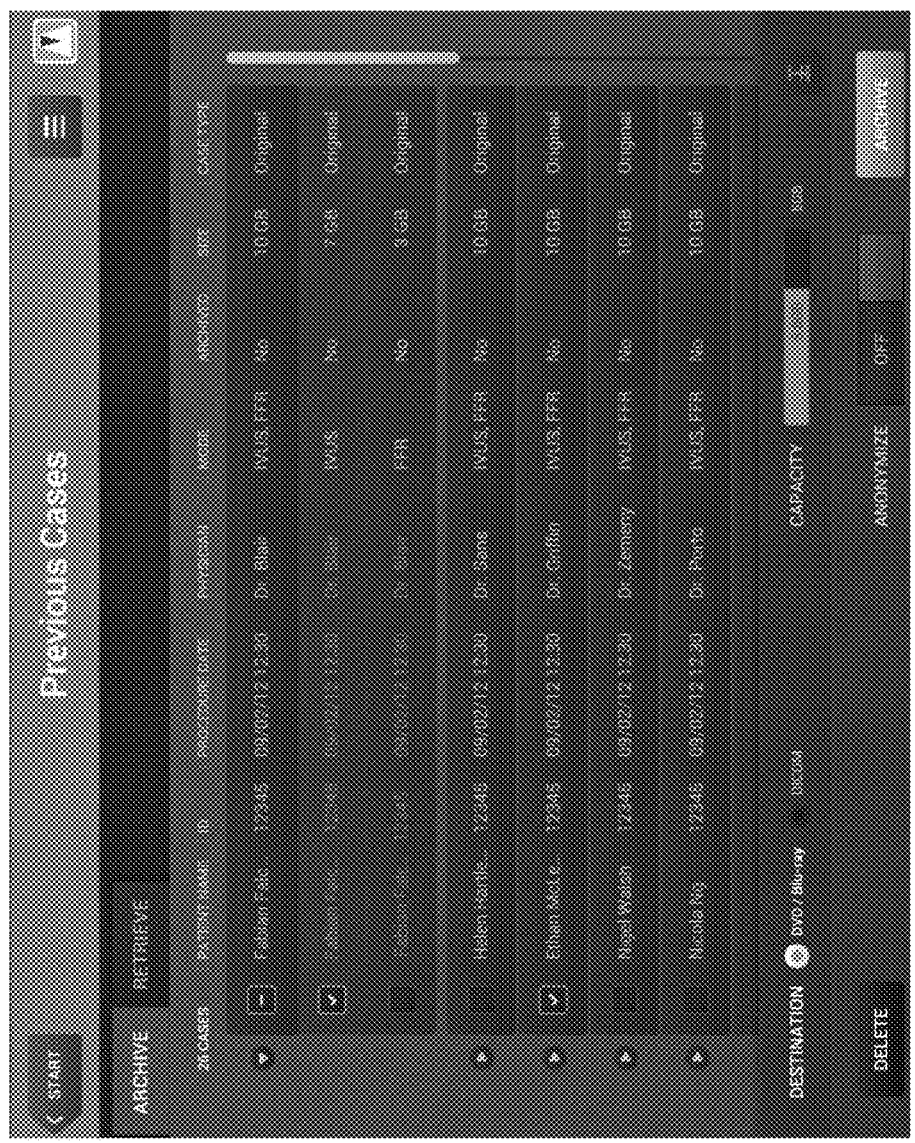
FIG. 15 is an example archival screen of the case management user interface rendered by the multi-modality processing system of FIG. 1.

Further, in some embodiments, the archival system of FIGS. 14 and 15 is configured to archive medical data to a location chosen by a practitioner, rather than a fixed location. For example, in the example screen 1400, a practitioner may choose to either archive to a removable medium such as an optical writable disc or portable flash storage, or archive to a networked remote storage medium such as a DICOM server. In alternative embodiments, additional and/or different archival locations may be selected by a practitioner such as a local hard drive, storage area network (SAN), or cloud-based storage.

In certain embodiments, the archival system of FIGS. 14 and 15 is configured to archive medical data in one of a plurality of different formats, as selected by a practitioner on the example screen 1400. In that regard, patient medical data may be simply archived "as is" without a format change, its format may be modified (i.e., to a format selected on screen 1400), or it may be archived in a compressed form to reduce the amount of required storage space. In one embodiment, the medical data may be inserted into a proprietary or industry-standard archival data container. Further, medical data archived by the illustrated archival system may be encrypted, or otherwise obfuscated to prevent unauthorized access. In some embodiments, an option to encrypt and/or limit access to an archived item via a password may be presented on the archival screen 1400.

The archival element of the multi-modality processing system 101 illustrated in the embodiment of FIGS. 14 and 15 is further configured to selectively anonymize medical data before it is archived. For example, a practitioner may choose whether to remove identifying patient information from medical data before it is archived. In more detail, when archiving a patient case without anonymizing, all acquired modality data sets and also all metadata—including identifying patient information—are included in the archive container. Similarly, an individual archived modality data set and images also would include identifying patient information if archived without anonymizing. However, if a practitioner chooses to anonymize before archiving, the archival system automatically removes any information from an archival record that could identify the patient from whom the data was acquired. In the illustrated embodiment, the archival system anonymizes medical data when an "Anonymize" button on the archival screen 1400 is actuated. Notably, the archival system is configured to remove all identifying patient information without the influence of the practitioner performing the archival. That is, the system first determines which data fields in a patient case contain information that could identify a patient, and then deletes any data in the identified fields. In one embodiment, the determination is based on a configuration file that includes a pre-determined set of data fields known to include identifying information. In an alternative embodiment, the archival system determines sensitive data fields on a case-by-case basis using natural language processing algorithms. Further, in some embodiments, identifying patient information is obfuscated, rather than removed, during the anonymizing procedure. In such an embodiment, obfuscated patient information may only be recovered by authorized systems or practitioners. Additionally, when multiple patient cases corresponding to multiple patients are selected for archive—and the anonymizing option is selected—identifying information about each different patient is removed or obfuscated from the patient cases.

Accordingly, because the multi-modality processing system 101 anonymizes archival data automatically without intervention by the practitioner, at least some of the removed patient information remains hidden from the practitioner or other third party data processor, thereby increasing confidentiality of sensitive medical information. Further, automated anonymization reduces clerical errors and ensures all identifying information is removed, regardless of whether it is accessible via the user interface. Further, in the archival scenario described herein, the anonymizing action is performed at the multi-modality acquisition/processing system itself before the data is transmitted to a remote archival storage location. For example, in those embodiments in which the multi-modality processing system is a portable processing system stationed in a catheter lab, a practitioner may acquire medical data from a patient, anonymize it, and archive it to a removal storage medium, such as a DVD, all within the catheter lab at the processing system.

With reference back to FIG. 14, after a practitioner has selected one or more patient cases, data sets, and/or images to archive, an archive request 1402 is transmitted to the MMCM workflow component 214. The archive request is indicative of the specific medical data selected to be archived and whether the selected medical data should be anonymized. The MMCM workflow component 214 processes the request and retrieves the selected medical data 1404 from the data repository 304. If the practitioner indicated that the medical data 1404 should be anonymized, patient identifying information 1406 is removed or obfuscated by the MMCM workflow component 214 before it is saved to the archival storage medium 316. The MMCM workflow component 214 may further modify the data to be archived such as by compressing it, encrypting it, changing its format, and/or placing it in an archival data container, etc.

It is understood that the system and method described above for archiving and anonymizing multi-modality medical data in a multi-modality processing system is simply an example embodiment, and in alternative embodiments, additional and/or different steps may be included in the method and the system may include additional and/or different user interface screens. Further, the archival screen 1400 is simply an example and it may include different and/or additional features and user options to further facilitate patient case management within the multi-modality processing system 101.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. And the processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of collecting multi-modality medical data associated with a patient and displaying the multi-modality medical data with a multi-modality medical processing system, the method comprising:
   receiving, with a first modality component of the multi-modality medical processing system, first medical data associated with a first medical modality and acquired from the patient from a first medical instrument positioned within a vessel of the patient, the first medical instrument comprising an intravascular catheter or guide wire including a flexible elongate member and a data collecting component configured to obtain the first medical data;
   associating the first medical data with a unique identifier for the patient;
   storing the first medical data in a data repository;
   receiving, with a second modality component of the multi-modality medical processing system, second medical data about the patient from a second medical instrument, the second medical data being associated with a second medical modality different than the first medical modality, wherein the first and second medical modalities are each one of intravascular ultrasound (IVUS), forward looking IVUS (FL-IVUS), intravascular photoacoustic (IVPA), pressure, flow, temperature, fractional flow reserve (FFR), instantaneous wave-free ratio (iFR), coronary flow reserve (CFR), optical coherence tomography (OCT), intracardiac echocardiography (ICE), forward-looking ICE (FLICE), intravascular palpography, transesophageal ultrasound, x-ray, magnetic resonance imaging (MRI), or computed tomography (CT), wherein a multi-modality management component is in communication with the first modality component and the second modality component;
   associating the second medical data with the unique identifier;
   storing the second medical data in the data repository;
   displaying a plurality of selectable options associated with the unique identifier, wherein the displaying includes displaying a first selectable option and a second selectable option simultaneously in a same portion of a user interface (UI) output region on a touch sensitive display of a bedside controller positioned proximate to the patient, wherein the first selectable option controls display of the first medical data and the second selectable option controls display of the second medical data, wherein the bedside controller is in communication with the first medical instrument, the second medical instrument, and the multi-modality medical processing system, wherein a UI component of the multi-modality medical processing system renders the touch sensitive display of the bedside controller, wherein the UI component is utilized by the multi-modality management component to display data associated with the first modality component and the second modality component;
   receiving a user selection of the first selectable option to display the first medical data, the user selection comprising a user input received on the touch sensitive display of the bedside controller; and
   displaying, in response to receiving the user selection, the first medical data in the user interface output region on the touch sensitive display of the bedside controller.

2. The method of claim 1, further including:
   receiving a further user selection of the second selectable option to display the second medical data; and
   displaying the first medical data and the second medical data concurrently in the user interface.

3. The method of claim 1, wherein displaying the first and second selectable options includes displaying the first and second selectable options in an order determined by a metadata value associated with the first medical data and the second medical data.

4. The method of claim 3, wherein the metadata value is one of medical modality, medical data acquisition time, or practitioner name.

5. The method of claim 1, wherein displaying the first and second selectable options includes displaying the first and second selectable options in groups based on the modality of the represented medical data.

6. The method of claim 1, further including displaying additional information about the first medical data upon receiving a user actuation of a toggle element associated with the first selectable option.

7. The method of claim 6, wherein the additional information includes a preview image of a portion of the patient derived from the first medical data.

8. The method of claim 6, wherein the additional information is displayed adjacent to the first selectable option.

9. The method of claim 6, wherein the additional information includes a pullback rate of an acquisition procedure that generated the first medical data.

10. The method of claim 1, further including:
displaying a delete button upon receiving a user actuation of a toggle element associated with the first selectable option;
receiving a user actuation of the delete button; and
deleting, in response to receiving the user actuation, the first medical data from the data repository.

11. The method of claim 1, wherein the first medical data and the second medical data were acquired from the patient during a single catheter lab session.

12. A multi-modality medical processing system, comprising:
a data repository;
a first medical instrument communicatively coupled to the multi-modality medical processing system and configured to be positioned within a vessel of a patient, the first medical instrument being sized and shaped for insertion into the vessel and comprising an intravascular catheter or guide wire including a flexible elongate member and a data collecting component configured to obtain first medical data associated with a first medical modality while positioned within the vessel of the patient;
a non-transitory, computer-readable storage medium that stores a plurality of instructions for execution by at least one computer processor, wherein the instructions are for:
receiving, with a first modality component of the multi-modality medical processing system, the first medical data acquired from the patient from the first medical instrument;
associating the first medical data with a unique identifier for the patient;
storing the first medical data in the data repository;
receiving, with a second modality component of the multi-modality medical processing system, second medical data acquired from the patient from a second medical instrument, the second medical data being associated with a second medical modality different than the first medical modality, wherein the first and second medical modalities are each one of intravascular ultrasound (IVUS), forward looking IVUS (FL-IVUS), intravascular photoacoustic (IVPA), pressure, flow, temperature, fractional flow reserve (FFR), instantaneous wave-free ratio (iFR), coronary flow reserve (CFR), optical coherence tomography (OCT), intracardiac echocardiography (ICE), forward-looking ICE (FLICE), intravascular palpography, transesophageal ultrasound, x-ray, magnetic resonance imaging (MRI), or computed tomography (CT), wherein a multi-modality management component is in communication with the first modality component and the second modality component; and
associating the second medical data with the unique identifier;
storing the second medical data in the data repository; and
a bedside controller positioned proximate to the patient, the bedside controller in communication with the first medical instrument, the second medical instrument, and the multi-modality medical processing system, the bedside controller comprising a touch sensitive display, wherein a user interface (UI) component of the multi-modality medical processing system renders the touch sensitive display of the bedside controller, wherein the UI component is in communication with the multi-modality management component such that the touch sensitive display is utilized by the multi-modality management component to display data associated with the first modality component and the second modality component, wherein the bedside controller is configured for:
displaying a plurality of selectable options associated with the unique identifier, wherein the displaying includes displaying a first selectable option and a second selectable option in a visual format simultaneously in a same portion of a user interface output region on the touch sensitive display of the bedside controller, wherein the first selectable option controls display of the first medical data and the second selectable option controls display of the second medical data;
receiving a user selection of the first selectable option to display the first medical data, the user selection comprising a user input received on the touch sensitive display of the bedside controller; and
displaying, in response to receiving the user selection, the first medical data in the user interface output region on the touch sensitive display of the bedside controller.

13. The multi-modality medical processing system of claim 12, wherein the instructions include further instructions for:
receiving a further user selection of the second selectable option; and
displaying the first medical data and the second medical data concurrently in the user interface.

14. The multi-modality medical processing system of claim 12, wherein displaying the first and second selectable options includes displaying the first and second selectable options in an order determined by a metadata value associated with the first medical data and the second medical data.

15. The multi-modality medical processing system of claim 14, wherein the metadata value is one of medical modality, medical data acquisition time, or practitioner name.

16. The multi-modality medical processing system of claim 12, wherein displaying the first and second selectable options includes displaying the first and second selectable options in groups based on the modality of the represented medical data.

17. The multi-modality medical processing system of claim 12, wherein the instructions include further instructions for displaying additional information about the first medical data upon receiving a user actuation of a toggle element associated with the first selectable option.

18. The multi-modality medical processing system of claim 17, wherein the additional information includes a preview image of a portion of the patient derived from the first medical data.

19. The multi-modality medical processing system of claim 17, wherein the additional information is displayed adjacent to the first selectable option.

20. The multi-modality medical processing system of claim 17, wherein the additional information includes a pullback rate of an acquisition procedure generating the first medical data.

21. The multi-modality medical processing system of claim 12, wherein the instructions include further instructions for:
   displaying a delete button upon receiving a user actuation of a toggle element associated with the first selectable option;
   receiving a user actuation of the delete button; and
   deleting, in response to receiving the user actuation, the first medical data from the data repository.

22. The multi-modality medical processing system of claim 12, wherein the first medical data and the second medical data were acquired from the patient during a single catheter lab session.

\* \* \* \* \*